United States Patent [19]

Freed

[11] 4,022,778

[45] May 10, 1977

[54] 10-ARYL-1,2,3,4-TETRAHYDROPYRAZINO(1,2-α)INDOLE AND DERIVATIVES THEREOF

[75] Inventor: Meier E. Freed, Paoli, Pa.

[73] Assignee: American Home Products Corporation, New York, N.Y.

[22] Filed: Nov. 5, 1971

[21] Appl. No.: 196,178

[52] U.S. Cl. .................. 260/250 BC; 260/239 BC; 260/239.3 T; 260/247.2 A; 260/268 TR; 260/293.59; 260/326.13 R; 260/326.34; 424/244; 424/248.54; 424/250; 424/267; 424/274

[51] Int. Cl.$^2$ ...................... C07D 403/06

[58] Field of Search ............. 260/326.13 R, 250 R, 260/239.3 T, 268 TR, 239 BC, 247.2 A, 250 BC, 293.59, 326.34

[56] References Cited

UNITED STATES PATENTS

| | | | |
|---|---|---|---|
| 3,660,430 | 5/1972 | Freed et al. ................. | 260/326.16 |
| 3,689,503 | 9/1972 | Reynolds et al. ......... | 260/326.13 R |

*Primary Examiner*—G. Thomas Todd

[57] ABSTRACT

Novel 10-aryl-1,2,3,4-tetrahydropyrazino(1,2-α)indole and derivatives and intermediates for their preparation are described, the products having anticonvulsant and central nervous system depressant activity.

11 Claims, No Drawings

10-ARYL-1,2,3,4-TETRAHYDROPYRAZINO(1,2-α)INDOLE AND DERIVATIVES THEREOF

This invention relates to novel 10-aryl-1,2,3,4 tetrahydropyrazino(1,2-a)indole and derivatives and intermediates for their preparation.

The final products of the present invention are represented by the general formula

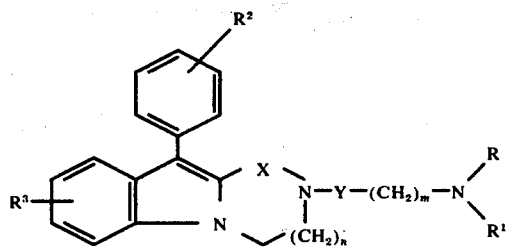

wherein X and/or Y is a member selected from the class consisting of $CH_2$ and

R and $R^1$ are each selected from the class consisting of hydrogen and (lower)alkyl; R and $R^1$ may be joined together to form a saturated heterocyclic ring containing one or two hetero atoms selected from the class consisting of nitrogen, oxygen and sulfur and having a total of five to seven ring members; $R^2$ and $R^3$ are each selected from the class consisting of hydrogen, (lower)alkyl, trifluoromethyl and halo; n is a whole number which is 1 or 2; m is a whole number from 1 to 3.

This invention also includes novel intermediates of the general formulae:

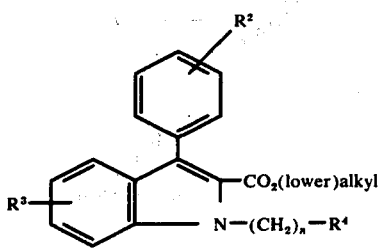

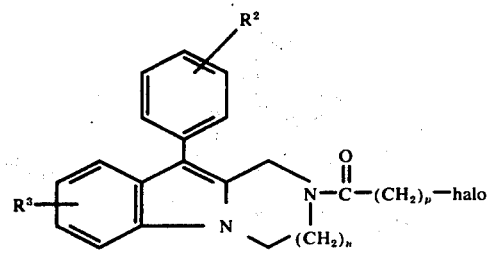

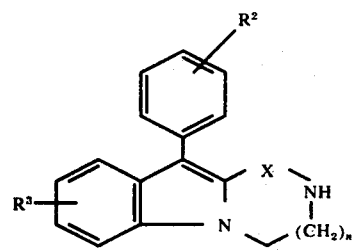

wherein $R^4$ is selected from the class consisting of CN and $CH_2NH_2$; p is a whole number from one through 3; X, $R^2$, $R^3$ and n have the same meaning as previously specified.

The term "lower alkyl" as used herein means both straight and branch chain of from one to six carbon atoms as illustrated by methyl, ethyl, butyl, isobutyl, pentyl, 1,1-dimethyl butyl, etc. The term "halo" means chlorine, bromine, fluorine and iodine. The heterocyclic radical formed by R and $R^1$ joined together are exemplified by piperidino, pyrrolidino, morpholino, piperazino, etc.

The products of this invention may be employed in the form of pharmaceutically acceptable acid addition salts such as the hydrochloride, hydrobromide, sulfate, sulfamate, sulfonate phosphate, acetate, citrate, maelate ascorbate, tartrate, benzoate, etc, fumarate, etc.

The final products of this invention can be prepared by different methods. One route is shown by the following reaction sequence:

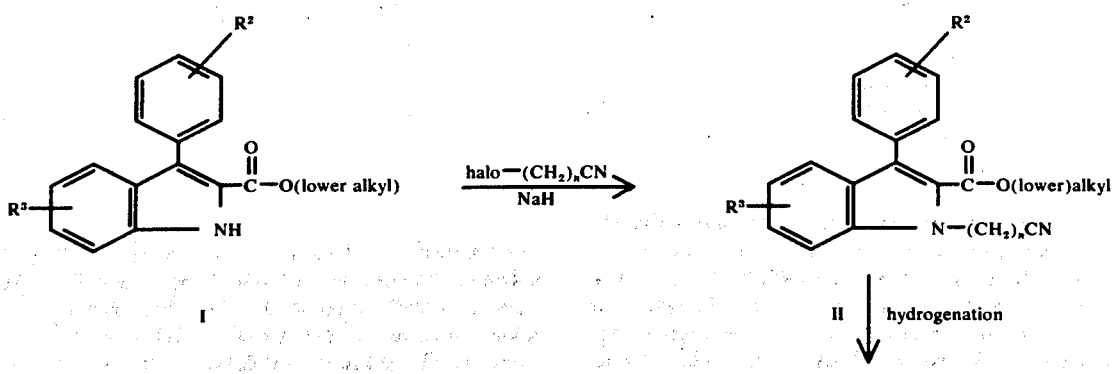

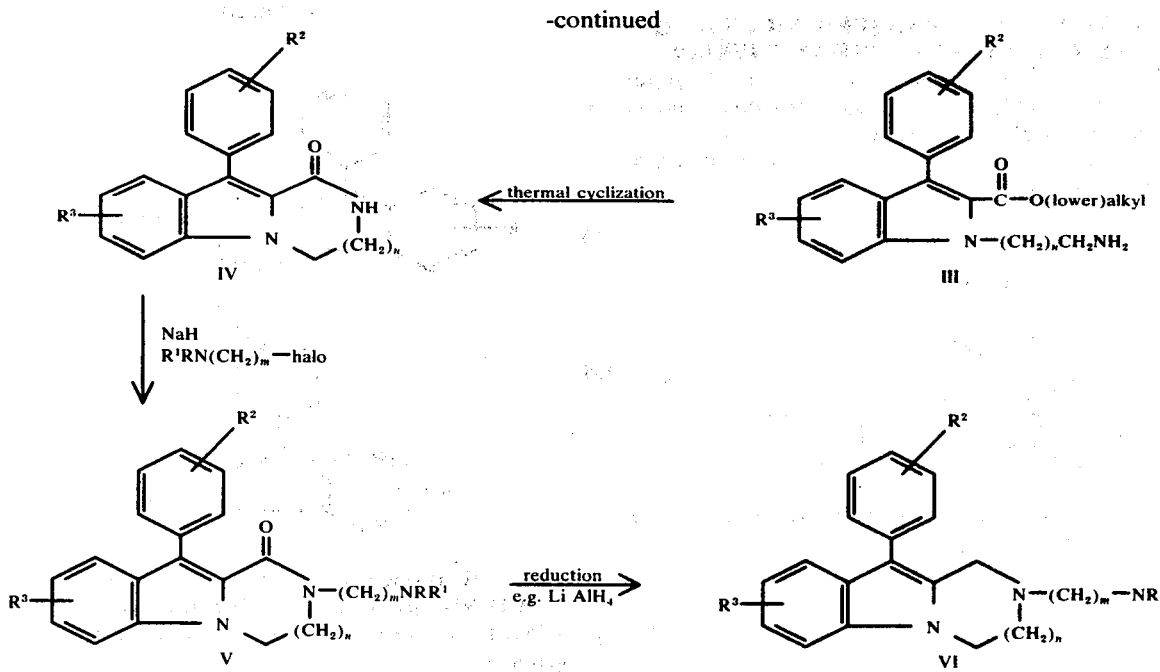

An alternate procedure for producing the compounds of formula VI is shown in the following reaction sequence:

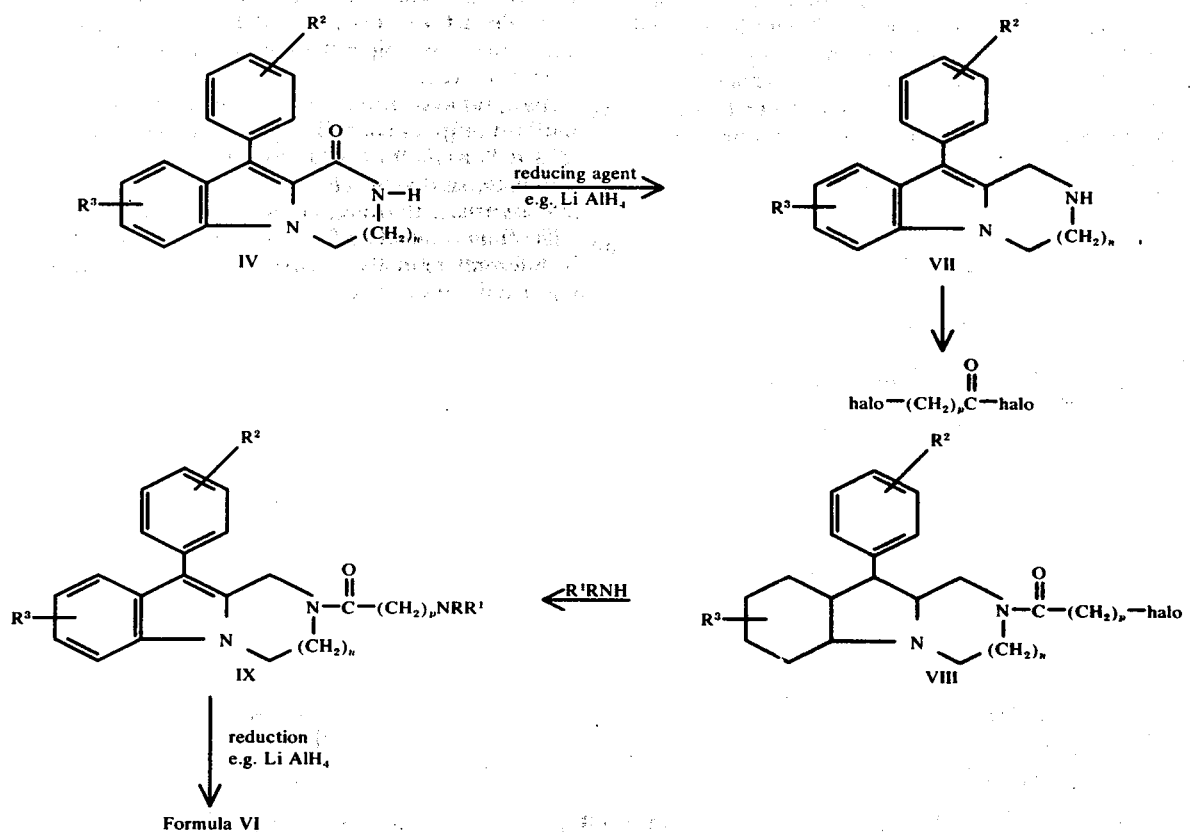

The compounds of formula V can be prepared directly in a single step from formula III by alkylation and cyclization using dimethyl sulfoxide and $RR^1N(CH_2)_m$-halo.

The starting materials of formula I can be obtained by several literature methods such as the Japp-Klingmann procedure followed by Fisher indolization. These starting materials may also be prepared by the method described in copending application Ser. No. 874,047 filed Nov. 4, 1969, the disclosure of which is incorporated herein by reference. This process comprises dissolving a 2-amino-benzophenone in an aprotic solvent, such as dimethylformamide, dimethylsulfoxide or sulfolane, and an α-halo acetate ester is added to the solution. The solution is quickly heated to a temperature of about 100° to 160° C. and maintained at that temperature for about 3 to 8 hours. Preferably, the solution is heated to reflux temperature and maintained at that temperature for about five hours. When the reaction is complete, the intermediate product, an N-(2-benzoyl)phenylglycinate ester is separated by standard recovery methods. For instance, the intermediate product may be removed by cooling and filtration, and purified by washing with water, drying and recrystallizing from an alkanol or a succession of alkanols.

In the second step, which is a base catalyzed cyclization, the reaction product of the first step is added to a basic condensing agent, such as sodium or potassium alkoxide (methoxide, ethoxide, t-butoxide) in an alkanol (such as methanol, ethanol, t-butanol) or sodium or potassium hydride and the like, in an inert organic solvent, such as benzene, toluene, tetrahydrofuran and the like. While catalysts containing other metals may be used, as is known in the art, sodium and potassium are preferred because they will dissolve in the solvents used in the reaction, and because they produce strong bases. The suspension is stirred at a temperature of about 10° to 50° C. for about 1 to 10 hours and allowed to stand. Preferably, the suspension is stirred at about 25° C. for about 6 hours and allowed to stand overnight.

When the reaction is complete the product a 3-phenylindol-2-yl-2-carboxylic acid ester of formula I is separated by standard recovery methods. For instance, the suspension may be cooled and the product filtered off, washed with water and dried. The solid material may be dissolved in hot benzene, toluene, benzenecyclohexane or aqueous ethanol, filtered and the filtrate concentrated and cooled affording the product.

The following examples are illustrative of the present invention.

EXAMPLE 1 ethyl 3-phenyl-5-chloroindole-2-carboxylate

To a freshly prepared solution of sodium ethoxide (from 6.44 g., 0.28 mole of sodium in 600 ml. of anhydrous ethanol), cooled to 10° C and well stirred, is added solid, finely divided ethyl N-(2-benzoyl-4-chloro phenyl glycinate (89 g., 0.38 mole). The suspension is stirred at 25° C. for 6 hours and allowed to stand overnight. The suspension is cooled to 10° C. and cold water (800 ml.) is added. The product is filtered off, washed several times with water and dried. This material is dissolved in 800 ml. of hot benzene, filtered concentrated to 400 ml., and cooled. The product weighs 29 g., a 34.5 percent of theoretical yield, and gives a melting point of 171°-172° C.

Anal. Calcd. for $C_{17}H_{14}NClO_2$: C, 68.40; H, 4.71; N, 4.70; Cl, 11.79. Found: C, 68.52; H, 4.58; N, 4.64; Cl, 12.07.

EXAMPLE 2

Ethyl 1-cyanomethyl-3-phenyl-5-chloroindole-2-carboxylate

To a suspension of sodium hydride (from 7.2 gms., 0.15 mole 50% sodium hydride dispersed in mineral oil) in 125 ml fresh dimethyl formamide (DMF) is added ethyl 3-phenyl-5-chloroindole-2-carboxylate (45 gms, 0.15 mole), as a dry powder, in portions. The reaction is exothermic and requires a water bath to maintain the temperature between 45°-50° C. After stirring 15-20 minutes (at 35° C), chloroacetonitrile (12 grams, 0.15 mole) in 25 ml DMF is added slowly. The temperature rises to 45° C and the mixture is stirred overnight at ambient temperature. The mixture is then transferred to a one liter beaker and 500 ml of ice-water is added slowly. After 15-20 minutes the product is filtered off, washed well with water, and dried on a Buchner funnel. After recrystallization from ethanol the product gives a m.p. of 117°-19° C. There is obtained a total of 46 grams (90.2%), of sufficient purity for the next step. A sample is recrystallized from aqueous ethanol, washed with water and vacuum dried, m.p. 119°-120° C.

Anal. Calcd for $C_{19}H_{15}ClN_2O_2$: C, 67.36; H, 4.46; N, 8.27; Cl, 10.46. Found: C, 67.10, H, 4.67; N, 8.22; Cl, 10.72.

EXAMPLE 3

Ethyl 1-(2-aminoethyl)-3-phenyl-5-chloroindole-2-carboxylate

A suspension of ethyl 1-cyanomethyl-3-phenyl-5-chloroindole-2-carboxylate (12 grams, 0.035 mole), and 0.15 grams of platinum dioxide in 200 ml absolute ethanol containing 45 ml of concentrated hydrochloric acid is shaken with hydrogen at 45 psi and 45° C, in a standard Parr apparatus. Hydrogenation is stopped after 5.5 lbs. of pressure drop is observed. After removal of catalyst by filtration the filtrate is taken to dryness under reduced pressure. The solid is stirred with water and refiltered and dried. This affords 13 grams of the hydrochloride, m.p. 196°-98° C. A sample is crystallized from ethanol, washed with acetone and dried. This material melts at 205°-206° C.

Anal. Calcd for $C_{19}H_{20}Cl_2N_2O$: C, 60.20; H, 5.31; N, 7.39; Cl, 18.68. Found: C, 60.14; H, 5.45; N, 7.40; Cl, 18.84.

EXAMPLE 4

8-Chloro-10-phenyl-1,2,3,4-tetrahydropyrazino[1,2-a]indole-1-one

Ethyl 1-cyanomethyl-3-phenyl-5-chloroindole-2-carboxylate (33.9 grams, 0.1 mole) is suspended in 250 ml ethanol containing dry hydrogen in a Parr apparatus with hydrogen at 45 psi and 45° C. After hydrogen uptake ceases (4 hours) the reaction mixture is allowed to cool. After removing the catalyst by filtration the filtrate is taken to dryness. The residue is stirred into the 1500 ml warm (40° C) water and solid potassium carbonate added until the solution is strongly basic. An oil is formed, which soon crystallizes. The solid is filtered off, dried, and redissolved in 600 ml xylene. To this solution is added 1 gram p-toluenesulfonic acid and the mixture is heated to reflux in a flask fitted with a Dean-Stark trap for water and ethanol removal. After 4 hours a clear solution is formed. The solvent is removed under vacuum and the residue treated with activated charcoal in benzene. Crystallization from benzene gives 15 grams (50.3%) of lactam, m.p. 235°-36° C. A sample of the above titled product recrystallized from acetone gives a m.p. of 239°-240° C.

Anal. Calcd for $C_{17}H_{13}N_2OCl$: C, 68.85; H, 9.45; N, 9.45; Cl, 11.94. Found: C, 68.85; H, 9.46; N, 9.30; Cl, 11.67.

EXAMPLE 5

8-Chloro-10-phenyl-1,2,3,4-tetrahydropyrazino[1,2-a]indole

To a stirred solution of lithium aluminum hydride (1 gram, 0.026 mole) in 20 ml dry tetrahydrofuran (THF) is added slowly a suspension of 1,2,3,4-tetrahydro-8-chloro-10-phenylpyrazino[1,2-a] indole-1-one (5.2 grams, 0.018 mole) in 40 ml of dry THF. This reaction mixture is stirred and refluxed for 8 hours after which it is cooled and decomposed by the slow addition of 3 ml of water. After stirring 1 hour the suspension is filtered. The filtercake is washed with isopropanol, THF, and acetone. The combined filtrate is taken to dryness and recrystallized from ethanol. The product is filtered off, washed with ether, and dried. The above titled product has a m.p. 163°–64° C. yield 4.5 grams (90%).

Anal. Calcd for $C_{17}H_{15}N_2Cl$: C, 72.35; H, 5.35; N, 9.92; Cl, 12.54. Found: C, 71.47; H, 5.37; N, 9.75; Cl, 12.80. Fumaric acid salt (from isopropanol) m.p. 224°–26° C.

Anal. Calcd for $C_{38}H_{34}N_4O_4Cl_2$: C, 67.00; H, 5.32; N, 8.23; Cl, 10.40. Found: C, 67.04; H, 5.10; N, 8.14; Cl, 10.75.

EXAMPLE 6

1,2,3,4-Tetrahydro-2-(3-dimethylaminopropyl)-8-chloro-10-phenylpyrazino[1,2-a]indole-1-one To a stirred solution of ethyl 3-phenyl-5-chloro-1-(2-aminoethyl)indole-2-carboxylate (6 grams, 0.019 mole) in 50 ml dimethyl formamide is added potassium carbonate, powdered, 3.4 grams (0.025 mole), followed by 2.45 grams (0.02 mole) distilled dimethylaminopropyl chloride. The solution is stirred 56 hours at room temperature, then heated at 100°–120° C. for 4 hours. After cooling, the suspension is poured into 200 ml ice-water and extracted with dichloromethane. The extract is washed with saline, then dried over sodium sulfate, filtered and concentrated. The residue, which contains considerable dimethyl formamide, is poured into water (300 ml). A solid is formed and is separated by decantation. The residue is crystallized from acetone.

After filtering and drying, the above titled product has a melting point 235°–36° C. A sample is converted to its hydrochloride. This material contains one water of crystallization and has a m.p. 232°–233° C.

Anal. Calcd for $C_{22}H_{25}ClN_3O$: C, 60.50; H, 6.24; N, 9.64; Cl, 16.28. Found: C, 60.21, H, 6.05; N, 9.55; Cl, 16.58.

EXAMPLE 7

1,2,3,4-Tetrahydro-2-dimethylaminopropyl-8-chloro-10-phenylpyrazino [1,2-a]indole-1-one A solution of 4.5 grams (0.015 mole) 8-chloro-10-phenyl-1,2,3,4-tetrahydropyrazino[1,2-a]indole-1-one in 30 ml DMF, is added to a suspension of sodium hydride (1 gram of 50% dispersion, 0.02 mole) in 20 ml DMF. After stirring at 34°–40° C for 20 minutes a solution of freshly distilled dimethylaminopropyl chloride (1.8 grams, 0.015 moles) in 5 ml DMF is added dropwise. Stirring is continued and the reaction mixture is heated at 50° C. for 8 hours. The mixture is cooled, and poured into cold water (300 ml). This is extracted 5 times with methylenedichloride. The extracts are washed well with saline. After drying the extract over sodium sulfate, the drying agent is filtered off and the filtrate is concentrated. The residue is diluted with ether. The product crystallizes out and is filtered off. Recrystallization from heptane gives 3.4 grams (62%) of above titled product, m.p. 151°–52° C.

Anal. Calcd for $C_{22}H_{24}ClN_3O$: C, 69.20; H, 6.32; N, 11.00. Found: C, 69.32; H, 6.00; N, 10.94.

EXAMPLE 8

2-(3-Dimethylaminopropyl)-8-chloro-10-phenyl-tetrahydropyrazino [1,2-a]indole

To a solution of sodium dihydro-bis-(2-methoxyethoxy) aluminate (4.04 grams, 0.02 mole) in 25 ml benzene, stirred magnetically, and warmed is added dropwise a solution of 2-dimethylaminopropyl tetrahydro-8-chloro-10-phenylpyrazino[1,2-a]indole-1-one (3.1 grams, 0.008 mole) in 35 ml of benzene. The reaction is stirred and heated to reflux. The solution turns a golden yellow which changes to orange, and then red. After 2 hours at reflux the mixture is cooled to ambient temperatures; the color fades to gold. Water (22 ml) is added and the reaction mixture stirred one hour. The benzene layer is removed and the aqueous layer reextracted with benzene and ether. The extracts are washed and dried over sodium sulfate. After concentration the residual oil is cooled and on standing solidifies, yielding 2.8 grams of the above titled product. The base (2.5 gms) is dissolved in acetone and added to a solution of fumaric acid (0.928 grams, 0.008 mole) in 60 ml acetone. The salt separates and is filtered off. This is washed with acetone, then ether. This material has a m.p. of 212°–214° C., yield 2.5g. Recrystallization from isopropanol affords 2.1 grams of the above titled product, as fumaric acid salt; m.p. 214°–215° C.

Anal. Calcd for $C_{26}H_{30}N_3O_4Cl$: C, 64.57; H, 6.26; N, 8.69. Found: C, 64.74; H, 6.34; N, 8.62.

EXAMPLE 9

2-Chloroacetamido-8-chloro-10-phenyl-1,2,3,4-tetrahydropyrazino [1,2-a]indole

A solution of chloracetyl chloride (4.60 g, 0.0407 mole) in dichloromethane (25 ml) is added over a period of three-fourth hours to a solution of 8chloro-10-phenyl-1,2,3,4-tetrahydropyrazino[1,2-a] indole (10.0 g, 0.0353 mole) and triethylamine (4.13 g, 0.0407 mole) in dichloromethane (100 ml). An exotherm raises the temperature to 39° C. The reaction mixture is stirred at room temperature for 6 hours, then allowed to stand overnight. It is concentrated to dryness. The residue was taken up in dichloromethane (500 ml), washed with water and saturated chloride solution and dried over anhydrous sodium sulfate. The drying agent is removed by filtration and the filtrate is concentrated to dryness. The residue is recrystallized twice from isopropanol, giving the above titled product, 6.94 g (54.7% yield), melting at 139°–149° C.

Anal. Calcd for $C_{19}H_{16}Cl_2N_2O$: C, 63.50; H, 4.49; Cl, 19.72; N, 7.80 Found: C, 63.08; H, 4.72; Cl, 19.46; N, 7.46.

EXAMPLE 10

8-Chloro-2-(diethylaminoacetyl)-1,2,3,4-tetrahydro-10-phenylpyrazino[1,2-a]indole A mixture of 2-chloroacetamido-8-chloro-10-phenyl-1,2,3,4-tetrahydropyrazino[1,2-a]indole (6.80 g, 0.0189 mole), diethylamine (3.46 g, 0.0473 mole) and sodium iodide (2.85 g, 0.019 mole) in ethanol (250 ml) is refluxed for 10 hours, then cooled to room temperature. The solid is removed by filtration and the filtrate is concentrated. The residue is taken up in dichloromethane (350 ml) and extracted with 10% hydrochloric acid (300 ml) in 4 portions. The dichloromethane solution is concentrated to a brown gummy residue. This is extracted with boiling water (500 ml), filtering off the insoluble material. The aqueous solution is basified to pH 10 with excess solid potassium carbonate. A solid is formed which is collected by filtration and is recrystallized from heptane, to give the above titled product, 5.30 g (70.9% yield) melting at 117°–119° C.

Anal. Calcd for $C_{23}H_{26}ClN_3O$: C, 69.80; H, 6.62; Cl, 8.95; N, 10.61. Found: C, 69.82; H, 6.39; Cl, 8.93; N, 10.43.

EXAMPLE 11

8-Chloro-2-diethylaminoethyl-10-phenyl-1,2,3,4-tetrahydropyrazino [1,2-]indole

A solution of 2-diethylacetamido-8-chloro-10-phenyl-1,2,3,4-tetrahydropyrazino-[1,2-a]indole (3.52 g. 0.00889 mole) in tetrahydrofuran (30 ml) is added dropwise to a suspension of lithium aluminum hydride (0.55 g. 0.0142 mole) in tetrahydrofuran (15 ml). The mixture is refluxed for 19½ hours, then cooled to room temperature. Water (2 ml) is added dropwise and the mixture is stirred for 5 hours, then filtered. The filtercake is washed first with tetrahydrofuran, then with methanol. The combined filtrate and washings are concentrated. The residue is extracted with ether. The ether solution is dried over anhydrous magnesium sulfate, filtered and concentrated to yield the above titled product as a yellow oil, 3.51 g.

A sample (2.7 g) of the oil in ether is converted to the dihydrochloride by treating its ethereal solution with a solution of hydrogen chloride in ether. The resulting solid is recrystallized from methanol-acetonitrile to give 0.54 g solid (17.3% yield), melting at 228°–231° C.

Anal. Calcd for $C_{23}H_{30}Cl_3N_3$: C, 60.70; H, 6.65; N, 9.24. Found: C, 60.41; H, 6.45; N, 9.00.

EXAMPLE 12

8-Chloro-10-phenyl-2-pyrrolidinoethyl-1,2,3,4-tetrahydropyrazino [1,2-a]indole-1-one A solution of 8-chloro-10-phenyl-1,2,3,4-tetrahydropyrazino-[1,2-a]indole-1-one (6.0 g, 0.0202 mole) in dimethyl formamide (40 ml) is added over a period of one-half hour to a suspension of sodium hydride (1.4 g, 0.029 mole of a 50% dispersion in mineral oil) in dimethylformamide (20 ml). The mixture is stirred at about 35° C. for 1 hour. A solution of freshly distilled N-($\beta$-chloroethyl)pyrrolidine (3.88 g, 0.029 mole) in dimethylformamide (10 ml) is added over a period of one-fourth hour. The reaction mixture is stirred at 50° C. for 18 hours, then cooled and poured into water (300 ml), this mixture is extracted with dichloromethane (4 portions, 100 ml each). The extracts are washed with saturated sodium chloride solution and dried over anhydrous sodium sulfate. The drying agent is removed by filtration and the filtrate is concentrated. The residue is recrystallized from heptane to give the above titled product, 6.15 g (77.3% yield), melting at 134°–135.5° C.

Anal. Calcd for $C_{23}H_{24}ClN_3O$: C, 70.15; H, 6.14; Cl, 9.00; N, 10.66 Found: C, 69.90; H, 6.09; Cl, 9.19; N, 10.52

Following the procedure described in the previous examples the following final products may be prepared:

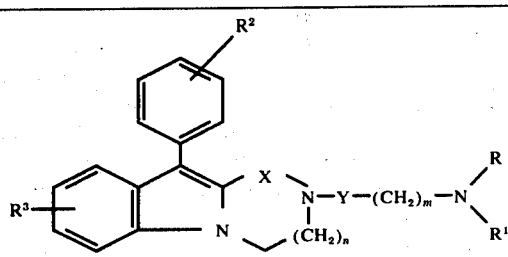

| Example | R and $R^1$ | R | $R^1$ | $R^2$ | $R^3$ | X | Y | n | m |
|---|---|---|---|---|---|---|---|---|---|
| 13-a | | H | H | Cl | H | $CH_2$ | $CH_2$ | 1 | 2 |
| b | | H | H | $CH_3$ | $CH_3$ | $\overset{O}{\underset{\|}{C}}$ | $CH_2$ | 2 | 1 |
| c | | $CH_3$ | $CH_3$ | H | H | $CH_2$ | $\overset{O}{\underset{\|}{C}}$ | 1 | 3 |
| d | | $C_2H_5$ | $C_2H_5$ | $CF_3$ | Cl | $CH_2$ | $CH_2$ | 2 | 2 |
| e | N⟩O | | | H | H | $CH_2$ | $\overset{O}{\underset{\|}{C}}$ | 1 | 2 |

In the pharmacological evaluation of the biological activity of the compounds of formulas IV – VII and IX, the in vivo effects are tested as follows. The compound is administered orally or intraperitoneally to three mice (14 to 24 grams) at each of the following doses: 400, 127, 40 and 12.7 milligrams per kilogram of host body weight (MPK). The animals are watched for a minimum of 2 hours during which time signs of general stimulation, (i.e., increased spontaneous motor activity, hyperactivity on tactile stimulation, twitching), general depression (i.e., decreased spontaneous motor activity, decreased respiration), autonomic activity (i.e., miosis, mydriasis, diarrhea) are noted.

The compounds of this invention induce central nervous system depressant effects and anticonvulant activity at a dose of 127 to 400 mg/kg.

When the compounds of this invention are employed as described above, they may be administered alone or in combination with pharmacologically acceptable carriers, the proportion of which is determined by the solubility and chemical nature of the compound, chosen route of administration and standard pharmacological practice. For example, they may be administered orally in the form of tablets or capsules containing such excipients as starch, milk, sugar, certain types of clay and so forth. They may be administered sublingually in the form of troches or lozenges in which the active ingredient is mixed with sugar and corn syrups; and then dehydrated sufficiently to make it suitable for pressing into a solid form. They may be administered orally in the form of solutions which may contain coloring and flavoring agents or they may be injected parenterally, that is intramuscularly, intravenously or subcutaneously. For parenteral administration they may be used in the form of a sterile solution containing other solutes, for example, enough saline or glucose to make the solution isotonic.

The dosage of the present therapeutic agents will vary with the form of administration and the particular compound chosen. Furthermore, it will vary with the particular subject under treatment. Generally, treatment is initiated with small dosages substantially less than the optimum dose of the compound. Thereafter, the dosage is increased by small increments until the optimum effect under the circumstances is reached. It will generally be found that when the composition is administered orally, larger quantities of the active agent will be required to produce the same effect as a smaller quantity given parenterally. In general, the compounds of this invention are most desirably administered at a concentration level that will generally afford effective results without causing any harmful or deleterious side effects.

What is claimed is:

1. A member selected from the class consisting of

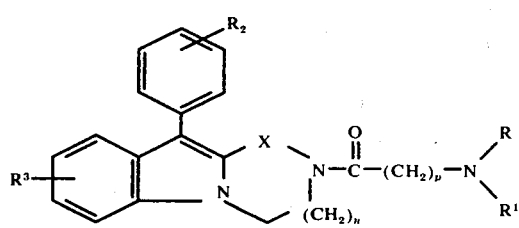

wherein:

X is $CH_2$; R and $R^1$ are selected from the class consisting of hydrogen and (lower)alkyl; R and $R^1$ when joined together form with the nitrogen atom a saturated heterocyclic ring selected from the class consisting of piperidino, pyrrolidino, morpholino and piperazino; $R^2$ and $R^3$ are selected from the class consisting of hydrogen, (lower)alkyl, $CF_3$ and halo; n is a whole number from 1 to 2; and p is a whole number from 1 through 3; and the nontoxic acid addition salts thereof.

2. A compound according to claim 1 which is: 8-chloro-2-(diethylaminoacetyl)-1,2,3,4-tetrahydro-10-phenylpyrazino[1,2-a] indole.

3. A compound which is: 8-chloro-10-phenyl-2-pyrrolidinoethyl-1,2,3,4-tetrahydropyrazino[1,2-a] indole-1one.

4. A member selected from the class consisting of

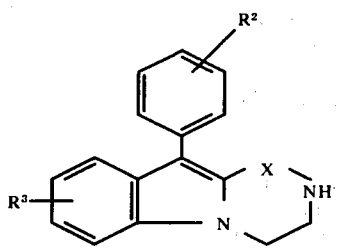

wherein S is selected from the class consisting of $CH_2$ and

$R^2$ is hydrogen and $R^3$ is selected from the class consisting of hydrogen, (lower)alkyl, and halo; and the nontoxic pharmaceutically acceptable acid addition salts thereof.

5. A compound according to claim 4 which is: 8-chloro-10-phenyl-1,2,3,4-tetrahydropyrazino[1,2-a]indole-1-one.

6. A compound according to claim 4 which is: 8-chloro-10-phenyl-1,2,3,4-tetrahydropyrazino[1,2-a]indole.

7. A member selected from the class consisting of

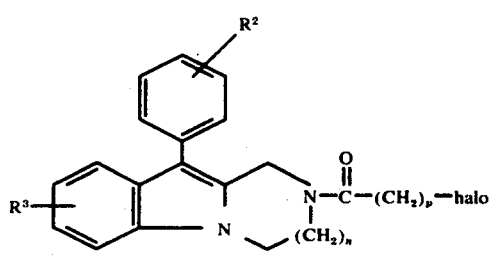

wherein $R^2$ and $R^3$ are selected from the class consisting of hydrogen, (lower)alkyl, $CF_3$ and halo; n is a whole number from 1 to 2; and p is a whole number from 1 through 3; and the nontoxic pharmaceutically acid addition salts thereof.

8. A compound according to claim 7 which is: 2-chloro-acetamido-8-chloro-10-phenyl-1,2,3,4-tetrahydropyrazino [1,2-a]indole.

9. A member selected from the class consisting of:

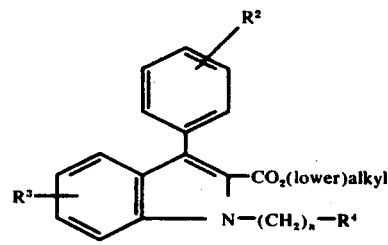

wherein $R^2$ is hydrogen and $R^3$ is selected from the class consisting of hydrogen, (lower)alkyl, and halo; $R^4$ is selected from the class consisting of CN and $CH_2NH_2$; and n is 1.

10. A compound according to claim 9 which is: ethyl 1-cyanomethyl-3-phenyl-5-chloroindole-2-carboxylate.

11. A compound according to claim 9 which is: ethyl 1-(2-aminoethyl)-3-phenyl-5-chloroindole-2-carboxylate.

* * * * *

UNITED STATES PATENT AND TRADEMARK OFFICE
CERTIFICATE OF CORRECTION

PATENT NO. : 4,022,778
DATED : May 10, 1977
INVENTOR(S) : Meier E. Freed

It is certified that error appears in the above-identified patent and that said Letters Patent are hereby corrected as shown below:

Claim 4 (Column 11), second line of text, change "S" to —X—.

Signed and Sealed this thirtieth Day of August 1977

[SEAL]

Attest:

RUTH C. MASON
*Attesting Officer*

C. MARSHALL DANN
*Commissioner of Patents and Trademarks*